(12) United States Patent
Otaki et al.

(10) Patent No.: US 11,882,355 B2
(45) Date of Patent: Jan. 23, 2024

(54) CONTROL APPARATUS AND MEDICAL OBSERVATION SYSTEM

(71) Applicant: Sony Olympus Medical Solutions Inc., Tokyo (JP)

(72) Inventors: Hisayoshi Otaki, Tokyo (JP); Hiroshi Ushiroda, Tokyo (JP)

(73) Assignee: SONY OLYMPUS MEDICAL SOLUTIONS INC., Toyko (JP)

(*) Notice: Subject to any disclaimer, the term of this patent is extended or adjusted under 35 U.S.C. 154(b) by 351 days.

(21) Appl. No.: 17/165,977

(22) Filed: Feb. 3, 2021

(65) Prior Publication Data
US 2021/0297583 A1    Sep. 23, 2021

(30) Foreign Application Priority Data

Mar. 17, 2020 (JP) ................................. 2020-046853

(51) Int. Cl.
*H04N 23/62* (2023.01)
*G10L 15/22* (2006.01)
(Continued)

(52) U.S. Cl.
CPC ............ *H04N 23/62* (2023.01); *A61B 17/00* (2013.01); *A61B 34/25* (2016.02); *A61B 90/37* (2016.02);
(Continued)

(58) Field of Classification Search
CPC ......... A61B 3/10; A61B 5/0077; A61B 17/00; A61B 34/10; A61B 34/20; A61B 34/25; A61B 34/30; A61B 34/74; A61B 90/20; A61B 90/25; A61B 90/30; A61B 90/37; A61B 2017/00203; A61B 2090/373; A61B 1/000094; A61B 1/00018; A61B 17/00234; A61B 90/35; A61F 9/007; F24F 11/75; G02B 21/0012; G02B 21/244;
(Continued)

(56) References Cited

U.S. PATENT DOCUMENTS 4,989,253 A * 1/1991 Liang ................. G02B 21/0012
704/E15.045
5,867,308 A * 2/1999 Pensel .................. G02B 21/365
359/368

(Continued)

FOREIGN PATENT DOCUMENTS

JP    2008302146 A    12/2008
JP    2018138140 A    9/2018
(Continued)

*Primary Examiner* — Gerald Gauthier
(74) *Attorney, Agent, or Firm* — XSENSUS LLP

(57) ABSTRACT

A control apparatus includes circuitry configured to: acquire an image signal generated by an imaging device configured to image an observation target; acquire an operation instruction made by a voice input; control a display device to display a plurality of images generated based on the image signal corresponding to an operating state of the imaging device, together with information related to the operating state, in a case where the operation instruction is an operation instruction related to imaging of the imaging device; and control to change the imaging device to an operating state corresponding to the image selected by a user among the plurality of images.

19 Claims, 11 Drawing Sheets

(51) Int. Cl.
  *H04N 7/18* (2006.01)
  *G10L 15/02* (2006.01)
  *A61B 34/00* (2016.01)
  *A61B 90/00* (2016.01)
  *A61B 17/00* (2006.01)
  *A61B 90/25* (2016.01)

(52) U.S. Cl.
  CPC .............. *G10L 15/02* (2013.01); *G10L 15/22* (2013.01); *H04N 7/183* (2013.01); *A61B 90/25* (2016.02); *A61B 2017/00203* (2013.01); *A61B 2090/373* (2016.02); *G10L 2015/025* (2013.01); *G10L 2015/223* (2013.01)

(58) Field of Classification Search
  CPC ... G02B 21/365; G02B 27/0172; G06F 3/084; G06F 3/167; G06T 3/4007; G06T 7/285; G06T 7/0012; G10L 15/02; G10L 15/22; G10L 2015/025; G10L 2015/223; G10L 15/00; G10L 15/07; H04N 7/183; H04N 23/62; H04N 23/633; H04N 23/00; H04N 23/632; G16H 30/20; H04Q 9/00
  See application file for complete search history.

(56) References Cited

U.S. PATENT DOCUMENTS

| | | | | |
|---|---|---|---|---|
| 6,076,061 | A * | 6/2000 | Kawasaki | G06F 3/167 704/E15.044 |
| 6,591,239 | B1 * | 7/2003 | McCall | A61B 90/35 704/E15.045 |
| 6,993,486 | B2 * | 1/2006 | Shimakawa | H04Q 9/00 704/E15.044 |
| 7,286,992 | B2 * | 10/2007 | Sander | G02B 21/0012 704/275 |
| 8,370,157 | B2 * | 2/2013 | Boregowda | G10L 15/07 704/226 |
| 9,041,847 | B2 * | 5/2015 | Son | H04N 23/632 348/333.02 |
| 10,595,716 | B2 * | 3/2020 | Nazareth | A61B 90/30 |
| 10,702,353 | B2 * | 7/2020 | Tesar | G02B 21/0012 |
| 11,048,072 | B1 * | 6/2021 | You | G06T 7/285 |
| 11,224,673 | B1 * | 1/2022 | Kellogg, Jr | F24F 11/75 |
| 11,553,969 | B1 * | 1/2023 | Lang | G06T 3/4007 |
| 2004/0243147 | A1 * | 12/2004 | Lipow | A61B 34/74 606/130 |
| 2009/0292540 | A1 * | 11/2009 | Liu | G10L 15/00 704/E15.005 |
| 2010/0100080 | A1 * | 4/2010 | Huculak | A61B 34/25 606/1 |
| 2016/0228204 | A1 * | 8/2016 | Quaid | A61B 34/10 |
| 2016/0242623 | A1 | 8/2016 | Pasini | |
| 2017/0196453 | A1 * | 7/2017 | Papac | A61B 3/10 |
| 2017/0212723 | A1 * | 7/2017 | Atarot | G06F 3/167 |
| 2018/0220100 | A1 * | 8/2018 | Ovchinnikov | G06F 3/0484 |
| 2018/0289428 | A1 * | 10/2018 | Lee | G02B 21/365 |
| 2019/0107700 | A1 * | 4/2019 | Lee | A61B 90/20 |
| 2019/0117318 | A1 * | 4/2019 | Charron | A61B 5/0077 |
| 2019/0261841 | A1 * | 8/2019 | Tamura | A61B 1/000094 |
| 2019/0307313 | A1 * | 10/2019 | Wade | A61B 90/361 |
| 2019/0328479 | A1 * | 10/2019 | Wada | G02B 21/0012 |
| 2020/0085282 | A1 * | 3/2020 | Wada | G02B 21/0012 |
| 2020/0113413 | A1 * | 4/2020 | Hayashi | A61B 1/00018 |
| 2021/0141597 | A1 * | 5/2021 | Atarot | A61B 34/30 |
| 2021/0186624 | A1 * | 6/2021 | Charles | A61F 9/007 |
| 2021/0278653 | A1 * | 9/2021 | Yamaguchi | G02B 21/0012 |
| 2021/0297583 | A1 * | 9/2021 | Otaki | H04N 23/633 |
| 2021/0382559 | A1 * | 12/2021 | Segev | H04N 23/62 |
| 2022/0401178 | A1 * | 12/2022 | Polchin | A61B 34/20 |
| 2023/0107680 | A1 * | 4/2023 | Lynch | G02B 21/244 356/479 |

FOREIGN PATENT DOCUMENTS

| | | |
|---|---|---|
| WO | WO-2018216302 A1 | 11/2018 |
| WO | WO-2018235420 A1 | 12/2018 |

* cited by examiner

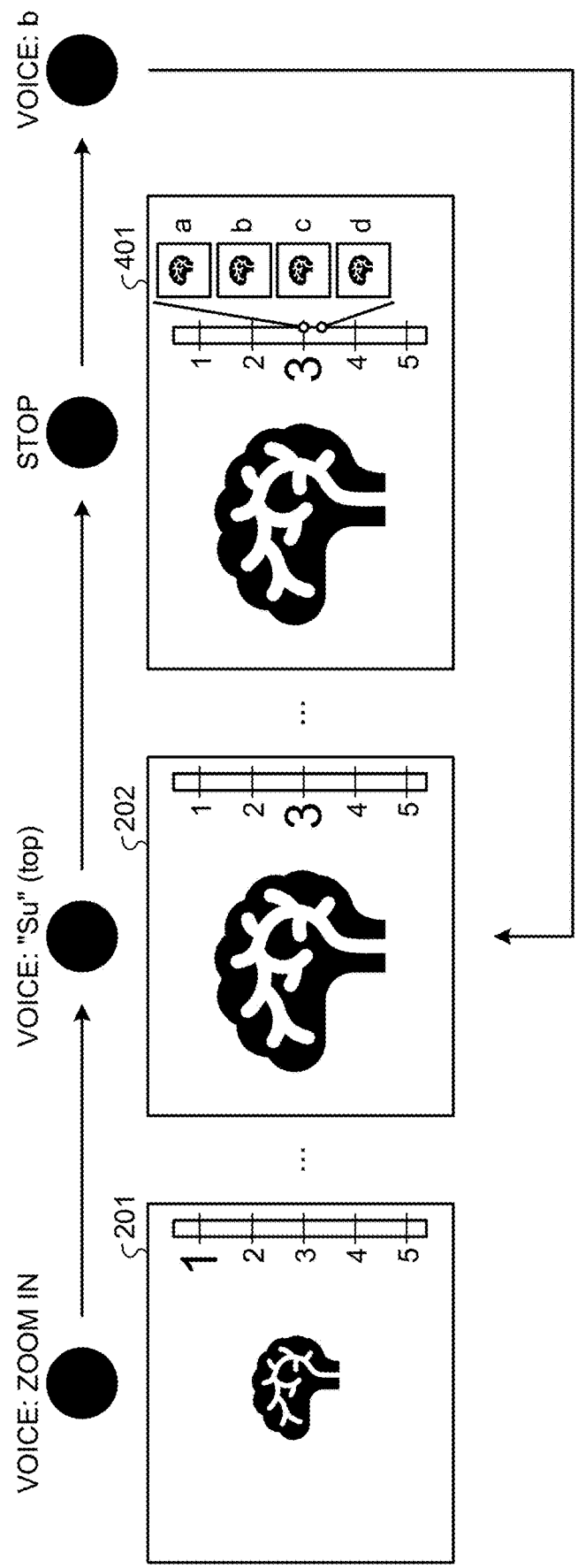

CONTROL APPARATUS AND MEDICAL OBSERVATION SYSTEM

CROSS-REFERENCE TO RELATED APPLICATION

This application claims priority from Japanese Application No. 2020-046853, filed on Mar. 17, 2020, the contents of which are incorporated by reference herein in its entirety.

BACKGROUND

The present disclosure relates to a control apparatus and a medical observation system.

There is known a medical observation system that magnifies and images a surgical site when performing surgery on the brain, heart, or the like of a patient as an observation target, and displays the captured image on a monitor (refer to JP 2016-42982 A, for example).

When a user such as a doctor inputs various operation instructions related to imaging, the user needs to operate a predetermined switch. During this operation, the user has to interrupt the surgery or change his/her posture, which is considered to be far from being efficient. To overcome this problem, it is conceivable that the user inputs voice and thereby gives various operation instructions related to imaging.

However, in the case of voice input, there would be requirements for the time, specifically, the time for the user to utter, the time for transmitting a voice signal to the control apparatus, the time for the control apparatus to recognize an instruction in the utterance, and the time for completing the operation. Due to these requirements, there would be a delay from the timing of the user utterance. Because of this delay, when the user attempts focusing using voice input, the focus lens would not stop at a position intended by the user, leading to a failure in the focusing.

To handle this, it is conceivable to employ a technique that achieves the processing intended by the user in consideration of the time difference between operation command timing intended by the user and operation command timing actually given by the user (for example, refer to JP 2001-175281 A).

SUMMARY

The above-described technique of JP 2001-175281 A has a problem of an increased load on the system due to complicated processes.

There is a need for a control apparatus and a medical observation system capable of performing processing with a low load when an operation instruction related to imaging is input by voice.

According to one aspect of the present disclosure, there is provided a control apparatus including circuitry configured to: acquire an image signal generated by an imaging device configured to image an observation target; acquire an operation instruction made by a voice input; control a display device to display a plurality of images generated based on the image signal corresponding to an operating state of the imaging device, together with information related to the operating state, in a case where the operation instruction is an operation instruction related to imaging of the imaging device; and control to change the imaging device to an operating state corresponding to the image selected by a user among the plurality of images.

BRIEF DESCRIPTION OF THE DRAWINGS

FIG. 11 is a diagram illustrating an outline of processing during a zoom operation performed by a medical observation system according to modification 2-1 of the second embodiment.

DETAILED DESCRIPTION

Hereinafter, embodiments (hereinafter, referred to as embodiments) will be described with reference to the attached drawings.

First Embodiment

Figure 1:
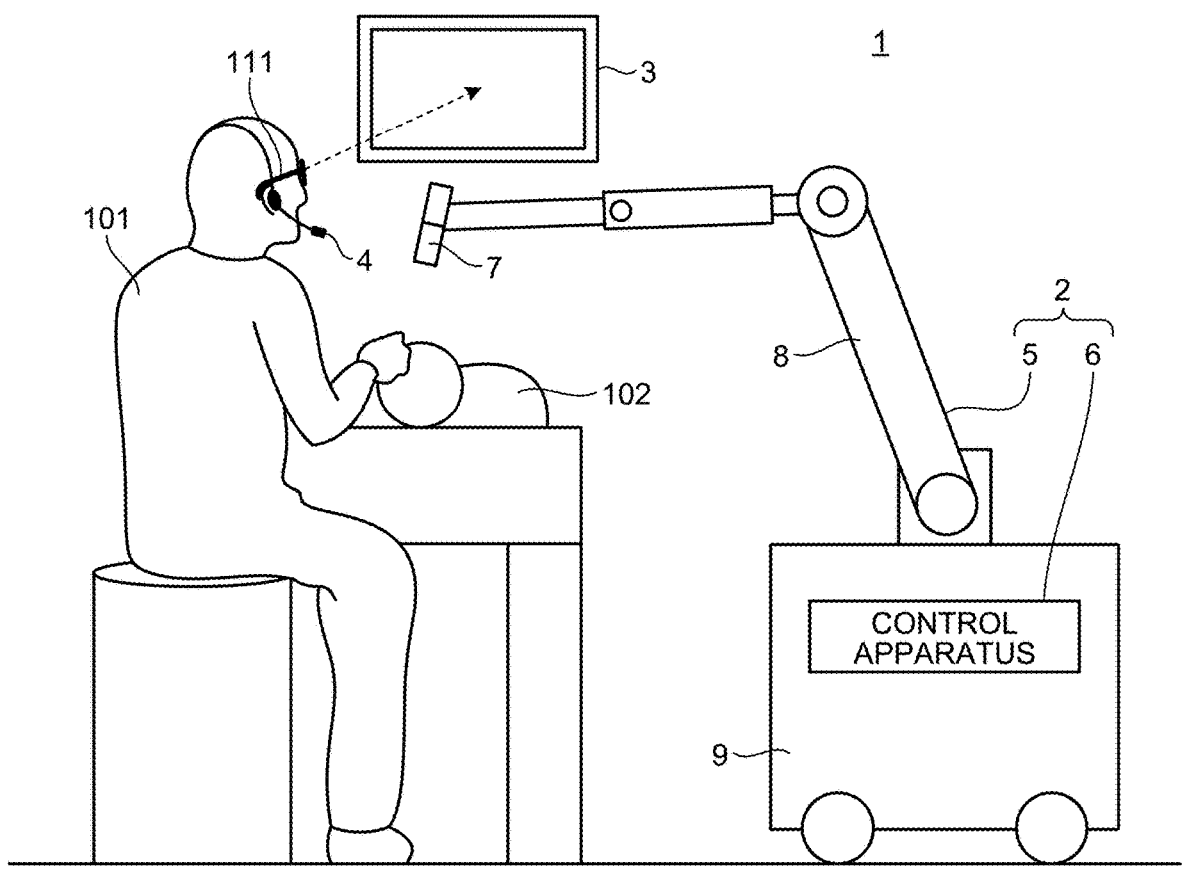
FIG. 1 is a diagram schematically illustrating a medical observation system according to a first embodiment.

FIG. 1 is a diagram schematically illustrating a medical observation system according to a first embodiment. FIG. 1 illustrates a situation in which a user 101 such as a doctor in charge of surgery using a medical observation system 1 is performing surgery of the head of a patient 102. The medical observation system 1 illustrated in FIG. 1 includes a medical observation apparatus 2, a display device 3, and a microphone 4.

The medical observation apparatus 2 is a surgical microscope, and includes a microscope apparatus 5 and a control apparatus 6. The microscope apparatus 5 has a function as an imaging device that images an observation target and generates an image signal.

Having a wireless or wired connection with the control apparatus 6, the display device 3 receives a three-dimensional image signal or a two-dimensional image signal from the control apparatus 6, and displays a three-dimensional image (3D image) based on the three-dimensional image signal or a two-dimensional image (2D image) based on the two-dimensional image signal. The display device 3 includes a display panel formed with liquid crystal or organic electro luminescence (EL). The display device 3 displays an image of the surgical site of the patient 102 captured in the imaging by the microscope apparatus 5. FIG. 1 schematically illustrates a situation in which the user 101 wearing 3D glasses 111 is visually observing a 3D image, which is displayed on the display device 3.

Having a wireless or wired connection with the control apparatus 6, the microphone 4 receives a voice input of the user 101, generates a voice signal, and transmits the generated voice signal to the control apparatus 6.

A visual configuration of the microscope apparatus 5 will be described. The microscope apparatus 5 includes a microscope unit 7 that magnifies and performs imaging of a microstructure of an observation target, a support 8 that supports the microscope unit 7, and a base 9 that holds a proximal end of the support 8 while incorporating the control apparatus 6.

The microscope unit 7 has a tubular portion having a columnar shape. On an aperture surface at a lower end of a main body, a cover slip is provided (not illustrated). The tubular portion has a size graspable by the user, and movable by the user while being grasped by the user when an imaging field of view of the microscope unit 7 is changed by the user. The shape of the tubular portion is not limited to the cylindrical shape, and may be a polygonal tubular shape.

The support 8 has a plurality of links on an arm unit, and the adjacent links are pivotably coupled to each other via joint portions. The support 8 includes, within an internal hollow portion, a transmission cable to transmit various signals between the microscope unit 7 and the control apparatus 6, and a light guide to transmit illumination light generated by the control apparatus 6 to the microscope unit 7.

The control apparatus 6 acquires a voice signal generated by the microphone 4 and recognizes information carried by the voice signal. In a case where the result of the recognition indicates that the information carried by the voice signal is an operating instruction related to the imaging of the microscope apparatus 5, data for displaying information related to the operating state of the microscope apparatus 5 will be generated and combined with the image signal so as to generate an image signal for display, which will be displayed on the display device 3. Furthermore, in a case where the information carried by the voice signal is an instruction to stop the operation of the microscope apparatus 5, the control apparatus 6 stops the operation. In a case where the information carried by the voice signal acquired after the stop is information designating the operating state of the microscope apparatus 5, the control apparatus 6 changes the microscope apparatus 5 to the operating state designated by the voice signal. The operation instruction related to the imaging of the microscope apparatus 5 is an operation instruction in any of focus, zoom, and visual field movement.

Figure 2:
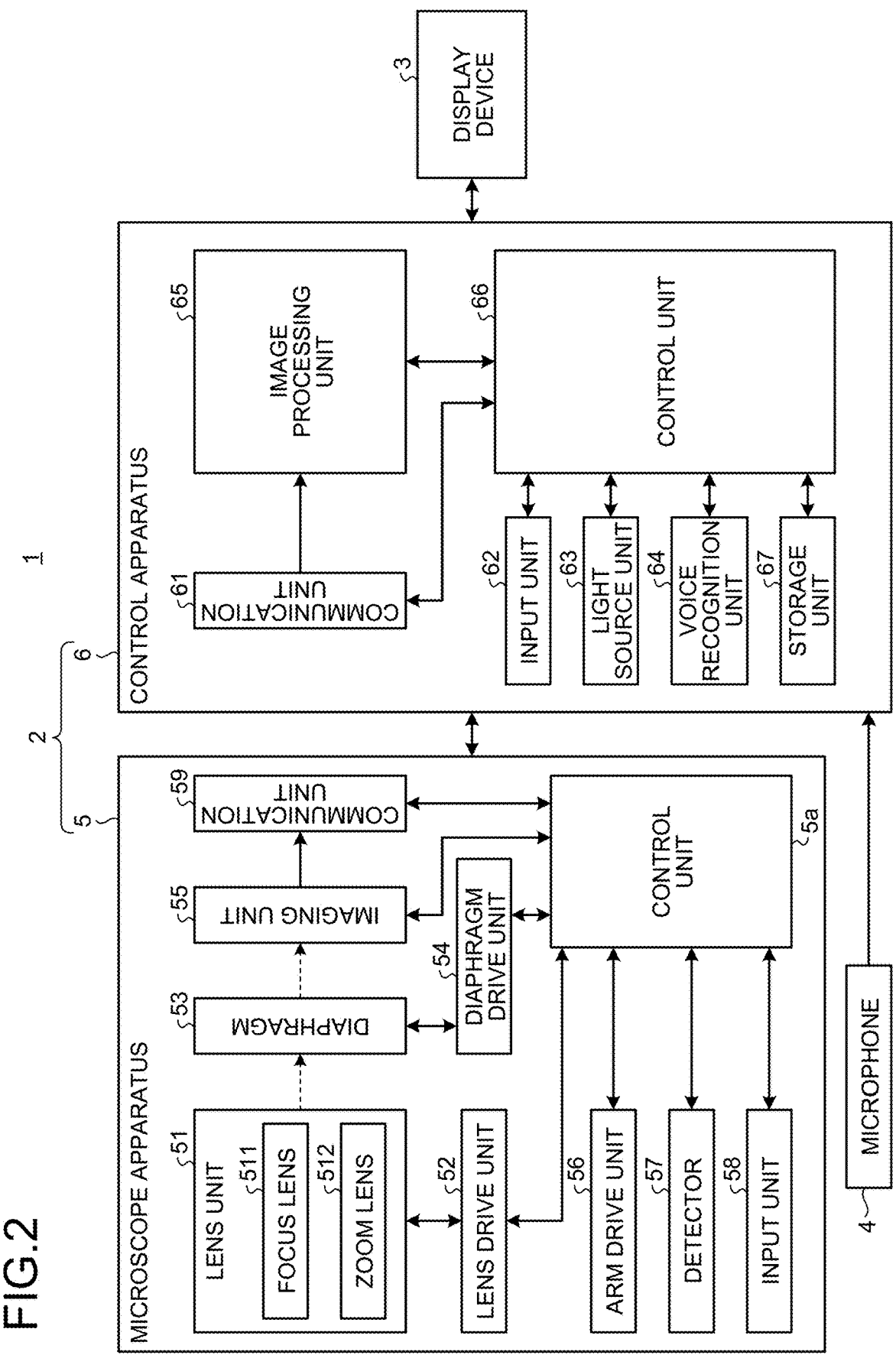
FIG. 2 is a block diagram illustrating a functional configuration of the medical observation system according to the first embodiment.

FIG. 2 is a block diagram illustrating the functional configuration of the medical observation system 1. First, the functional configuration of the microscope apparatus 5 will be described. The microscope apparatus 5 includes a lens unit 51, a lens drive unit 52, a diaphragm 53, a diaphragm drive unit 54, an imaging unit 55, an arm drive unit 56, a detector 57, an input unit 58, a communication unit 59, and a control unit 5*a*.

The lens unit 51 is an optical system that includes a plurality of lenses movable along an optical axis and that forms a condensed subject image on an imaging surface of an image sensor included in the imaging unit 55. The lens unit 51 includes a focus lens 511 that adjusts the focus and a zoom lens 512 that changes the angle of view. The focus lens 511 and the zoom lens 512 each include one or more lenses.

The lens drive unit 52 includes: an actuator that moves the focus lens 511 and the zoom lens 512 individually; and a driver that drives the actuator under the control of the control unit 5*a*.

The diaphragm 53 is provided between the lens unit 51 and the imaging unit 55, and adjusts the amount of light for the subject image from the lens unit 51 toward the imaging unit 55 under the control of the control unit 5*a*. The diaphragm 53, together with the lens unit 51, constitutes the optical system of the microscope apparatus 5.

The diaphragm drive unit 54 operates the diaphragm 53 under the control of the control unit 5*a* to adjust an aperture value (also referred to as an F-number).

The imaging unit 55 includes: an image sensor that forms an image from the subject image condensed by the lens unit 51 to generate a captured image (analog signal); and a signal processing unit that performs signal processing such as noise removal or A/D conversion on the image signal (analog signal) from the image sensor. The image sensor is formed with a complementary metal oxide semiconductor (CMOS) image sensor or a charge coupled device (CCD) image sensor, or the like. The imaging unit 55 may have two image sensors. In this case, the imaging unit 55 may generate an image signal of a three-dimensional image (3D image).

The arm drive unit 56 allows a plurality of joints of the support 8 to operate under the control of the control unit 5*a*. Specifically, the arm drive unit 56 includes: an actuator provided at a joint portion between the arms; and a driver to drive the actuator.

The detector 57 sequentially detects state information of the microscope apparatus 5. Examples of the state information of the microscope apparatus 5 include positions of the focus lens 511, the zoom lens 512, the imaging unit 55, and the joint portion of the support 8, the aperture value of the diaphragm 53, or the like. The detector 57 has various sensors for detecting the state information of the microscope apparatus 5.

The input unit 58 receives inputs such as an operation signal of the lens unit 51 and an arm operation signal for the support 8. The input unit 58 has a plurality of switches, buttons, or the like provided at positions on the side surface of the tubular portion of the microscope unit 7 where the user may perform operation while holding the microscope unit 7.

The communication unit 59 is an interface for communicating with the control apparatus 6. The communication unit 59 transmits an image signal (digital signal) generated by the imaging unit 55 to the control apparatus 6, and also receives a control signal from the control apparatus 6.

The control unit 5*a* controls the operation of the microscope apparatus 5 in cooperation with a control unit 66 of the control apparatus 6. The control unit 5*a* controls the microscope apparatus 5 to operate based on an operation instruction signal that the input unit 58 receives the input and the operation instruction signal transmitted from the control unit 66 of the control apparatus 6. In the present embodiment, a signal for allowing operation of the arm to move the imaging field of view of the microscope apparatus 5 is received from the control unit 66 of the control apparatus 6.

The control unit 5*a* includes at least one of processors such as a central processing unit (CPU), a field programmable gate array (FPGA), and an application specific integrated circuit (ASIC).

Next, the functional configuration of the control apparatus 6 will be described. The control apparatus 6 includes a communication unit 61, an input unit 62, a light source unit 63, a voice recognition unit 64, an image processing unit 65, a control unit 66, and a storage unit 67. The communication unit 61 acquires an image signal captured in the imaging by the microscope apparatus 5 and transmitted via a transmission cable. The image signal includes information related to imaging, such as a gain adjustment value at the time of imaging, a focus lens position, a zoom lens position, a shutter speed, and an aperture value. Furthermore, the communication unit 61 acquires an operation instruction using a voice signal of the user 101 an input of which has been received by the microphone 4. In this sense, the communication unit 61 has functions of an image signal acquisition unit and an operation instruction acquisition unit.

The input unit 62 receives inputs of various types of information. The input unit 62 is implemented by using a user interface such as a keyboard, a mouse, a touch panel, or a foot switch. The input unit 62 may have at least a part of the functions of the input unit 58 of the microscope apparatus 5.

The light source unit 63 generates illumination light to be supplied to the microscope apparatus 5 via a light guide. The light source unit 63 includes a solid-state light emitting element such as a light emitting diode (LED) or a laser diode (LD), a laser light source, a xenon lamp, a halogen lamp, or the like.

The voice recognition unit 64 executes a recognition process on the voice signal received from the microphone 4. By comparing the feature data of the voice signal with the feature data stored in the storage unit 67, the voice recognition unit 64 recognizes information carried by the voice signal. Examples of information recognized by the voice recognition unit 64 include an expression that gives an operating instruction regarding imaging of the microscope apparatus 5 and an expression that gives an instruction to stop an operation. For example, in a case where the operation is a focus operation, exemplary expressions that give the operating instruction are "focus in" and "focus out". Moreover, in a case where the operation is a zoom operation, exemplary expressions that give the operating instruction are "zoom in" and "zoom out". In addition, in a case where the operation is visual field movement, exemplary expressions that give the operating instruction are "move to the right", "move to the left", "move up", and "move down". Furthermore, an instruction to stop an operation is "stop". Note that this expression is only an example, and other expressions may be used.

The image processing unit 65 performs various signal processing on the image signal acquired by the communication unit 61. Specific examples of image processing performed when the image processing unit 65 generates an image signal for display include known types of image processing such as a detection process of brightness levels and contrast of an image signal, gain adjustment, interpolation processing, color correction processing, color enhancement processing, and contour enhancement processing. Furthermore, when the information carried by the voice signal recognized by the voice recognition unit 64 is an operating instruction regarding imaging of the microscope apparatus 5, the image processing unit 65 generates data for displaying information related to the operating state of the microscope apparatus 5 and combines the generated data for display with an image signal so as to generate an image signal for display. Details of the data for display will be described below with reference to FIGS. 3 to 5. The image processing unit 65 includes at least one of the processors such as a CPU, an FPGA, and an ASIC.

The control unit 66 controls the operation of the control apparatus 6 as well as performing comprehensive control of the operation of the medical observation apparatus 2 in cooperation with the control unit 5a of the microscope apparatus 5. In a case where the operation instruction is an operation instruction related to the imaging of the microscope apparatus 5, the control unit 66 controls to display a plurality of images generated based on the image signal corresponding to the operating state on the display device 3 together with information related to the operating state of the microscope apparatus 5. In addition, the control unit 66 controls the microscope apparatus 5 to be changed to an operating state corresponding to an image selected by the user among the plurality of images.

The control unit 66 generates a control signal for operating the microscope apparatus 5 based on the information carried by the voice signal recognized by the voice recognition unit 64, and transmits the generated control signal to the microscope apparatus 5. In order to set a brightness level of the image signal obtained by imaging by the microscope apparatus 5 to a predetermined brightness level, the control unit 66 performs control such as the shutter speed of the imaging unit 55, a gain adjustment performed by the image processing unit 65, and the amount of illumination light generated by the light source unit 63. Furthermore, the control unit 66 controls the display of the display device 3.

The control unit 66 includes at least one of processors such as a CPU, an FPGA, and an ASIC. The image processing unit 65 and the control unit 66 may use one processor as a common processor.

The storage unit 67 stores a return amount in a return mode. This return amount is preliminarily set in accordance with the depth of focus of a predetermined magnification. The predetermined magnification is higher than the magnification of the center of the settable range among the magnifications settable for the lens unit 51 of the microscope apparatus 5. Furthermore, the return amount may be half or less of the depth of focus.

The storage unit 67 stores various programs needed for operation of the control apparatus 6, and temporarily stores the data under arithmetic processing performed by the control apparatus 6. The storage unit 67 includes random access memory (RAM), read only memory (ROM), or the like.

Figure 3:
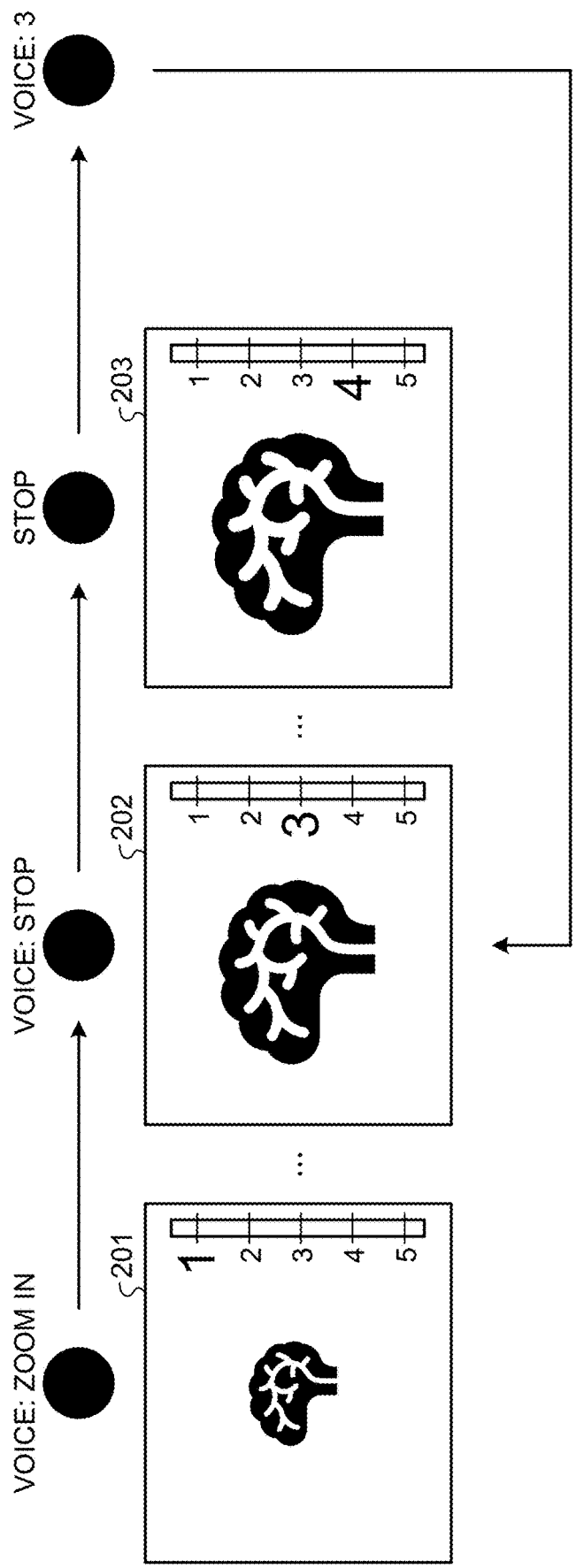
FIG. 3 is a diagram illustrating an outline of processing during a zoom operation performed by the medical observation system according to the first embodiment.

FIG. 3 is a diagram illustrating an outline of processing performed by the medical observation system 1. FIG. 3 schematically illustrates a change in the content to be displayed by the display device 3 when the user 101 performs a voice input of an instruction to activate the zoom function of the microscope apparatus 5 to increase the zoom magnification, to the microphone 4. In addition to the image captured by the microscope apparatus 5, the display device 3 displays classified position information of the zoom lens 512 being an operating target as information related to a zoom state, which is an operating state of the microscope apparatus 5, on the right side of the screen as On-Screen Display (OSD). This OSD display corresponds to the data for display generated by the image processing unit 65. Accordingly, images 201 to 203 illustrated in FIG. 3 are images corresponding to the image signals for display generated by the image processing unit 65. In the images 201 to 203, the class number indicating the zoom state at the time of capturing the image is displayed in larger in font size, than the other class numbers. For example, the image 201 illustrates that the zoom state is class 1.

When the user 101 inputs "zoom in" to the microphone 4, the control apparatus 6 causes the microscope apparatus 5 to perform a zoom operation to increase the zoom magnification, while causing the display device 3 to display the image 201 displaying information related to the zoom state in addition to the image of the subject. In accordance with the zoom operation, the zoom state changes sequentially from class 1 to classes 2, 3, and 4. FIG. 3 illustrates a case where the user 101 inputs "stop", which is an instruction to stop the zoom operation, to the microphone 4 when the user 101 views the image 202 having a zoom state of class 3. After the input of the stop instruction, there is a time lag before the microscope apparatus 5 actually stops the zoom operation. Therefore, in the case illustrated in FIG. 3, the zoom state in the image 203 at the stop of the zoom operation is class 4.

After the zoom operation of the microscope apparatus 5 is stopped, the user 101 inputs "3" to the microphone 4 in order to return the zoom state to the desired class 3. In response to this voice input, the control apparatus 6 returns the zoom state of the microscope apparatus 5 to class 3. In FIG. 3, the arrow from "voice: 3" to the image 202 merely indicates returning the zoom state of the microscope apparatus 5 to the class 3, and does not indicate redisplay of the image 202. Note that the user 101 needs to input a desired class number to the microphone 4 by voice, and does not need to input the same class number as the class number when the stop instruction is input.

Figure 4:
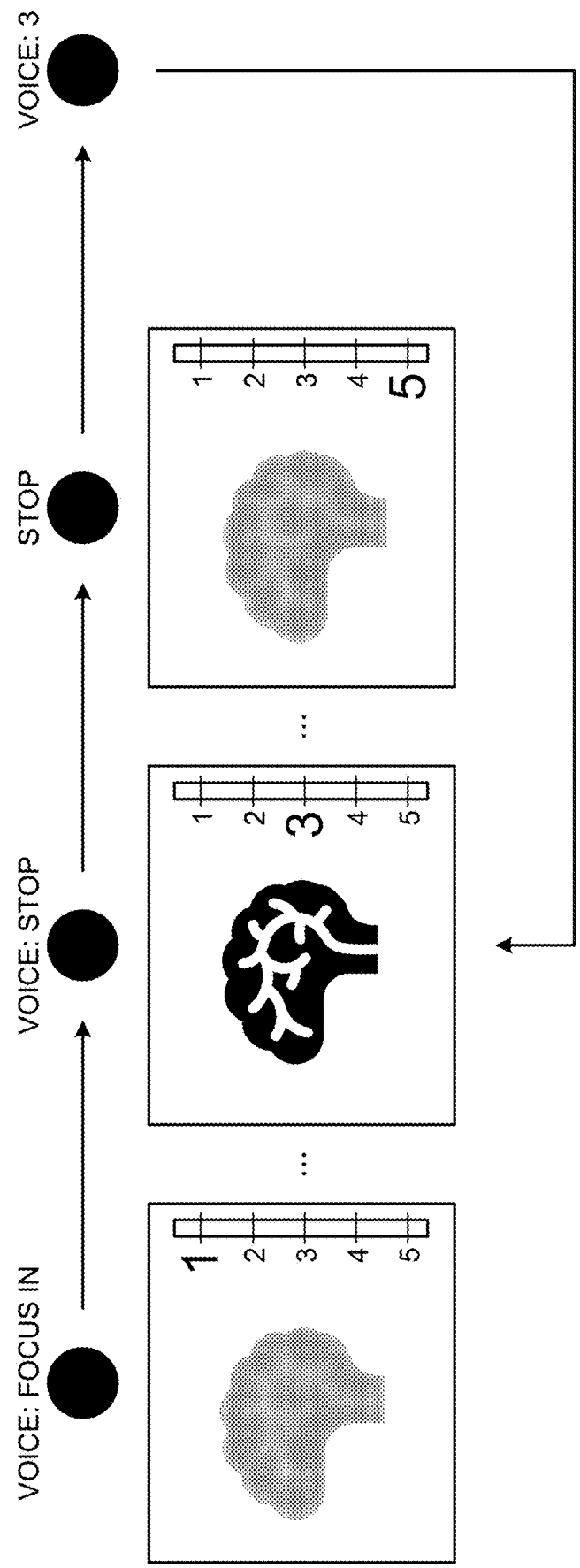
FIG. 4 is a diagram illustrating an outline of processing during a focus operation performed by the medical observation system according to the first embodiment.
Figure 5:
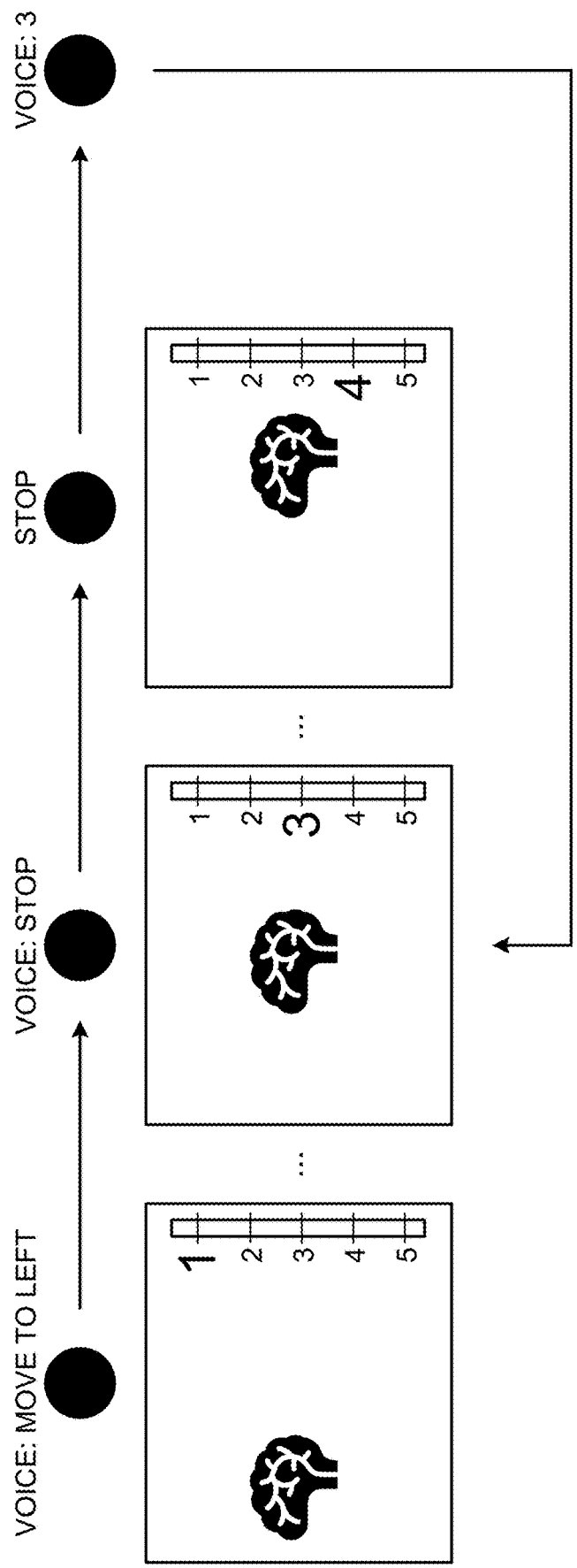
FIG. 5 is a diagram illustrating an outline of processing at the time of visual field movement performed by the medical observation system according to the first embodiment.

FIGS. 4 and 5 are diagrams illustrating an outline of the processing performed by the medical observation system 1 when the operations of the microscope apparatus 5 are focus operation and visual field movement, respectively.

FIG. 4 illustrates a case where the user 101 inputs "focus in" to the microphone 4, while FIG. 5 illustrates a case where the user 101 inputs "move to the left" to the microphone 4. As information on the operating state, FIG. 4 displays information indicating classified position information of the focus lens 511, which is the operating target, while FIG. 5 displays information indicating classified visual field information of the imaging unit 55, which is the operating target. Similarly to FIG. 3, FIGS. 4 and 5 also illustrate a case where the operating state when the user 101 inputs the stop instruction is class 3 and where the user 101 inputs "3" to the microphone 4 after the stop of operation. In the case of the visual field movement, an index indicating the center of the screen may be displayed. Furthermore, the user 101 may be allowed to perform selective input whether or not to display the index via the input units 58, 62 or the microphone 4.

Figure 6:
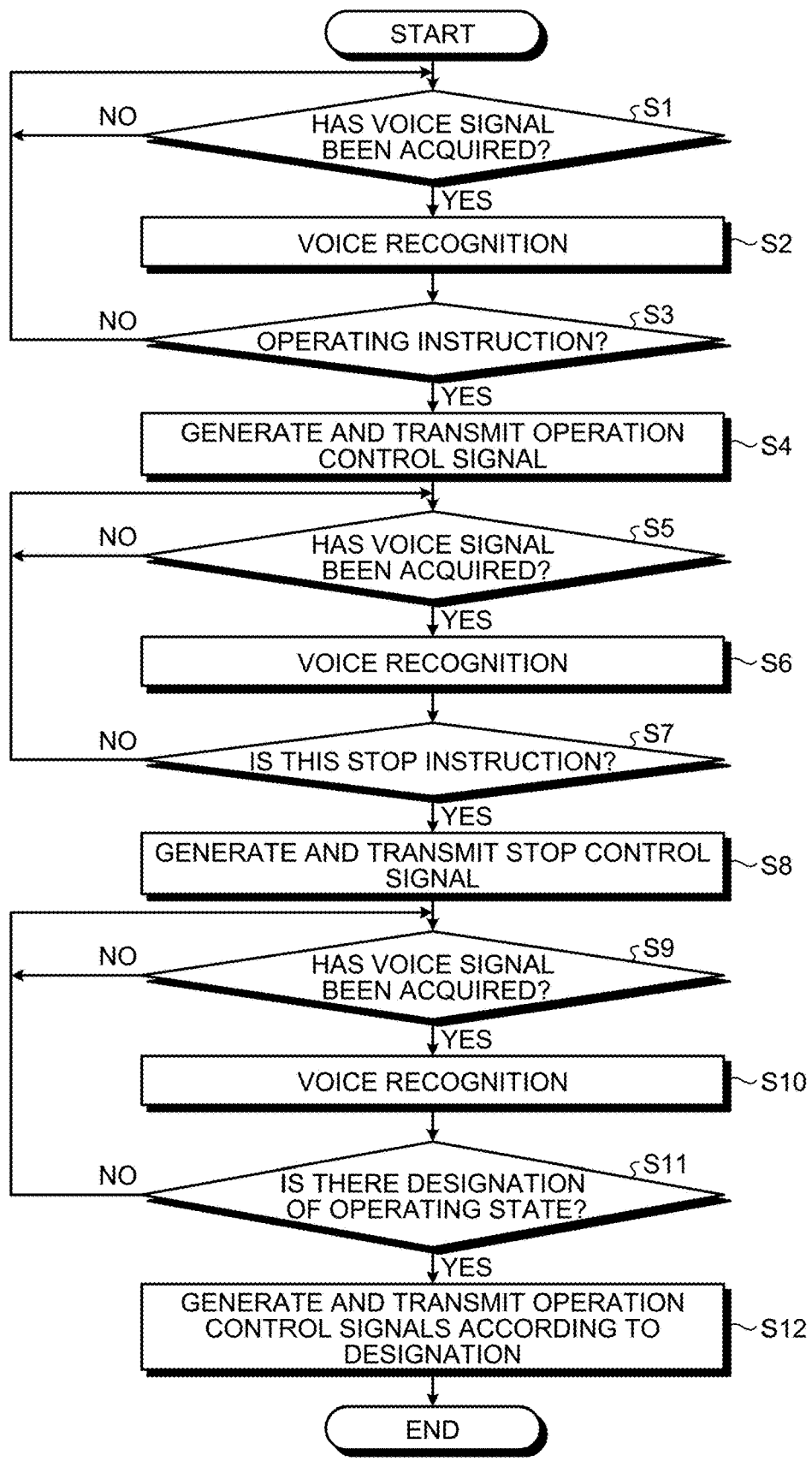
FIG. 6 is a flowchart illustrating an outline of processing of controlling a microscope apparatus performed by a control apparatus according to the first embodiment.

FIG. 6 is a flowchart illustrating an outline of processing of controlling the microscope apparatus 5 performed by the control apparatus 6. First, after the communication unit 61 acquires a voice signal (step S1: Yes), the voice recognition unit 64 performs a voice signal recognition process (step S2). In a case where the communication unit 61 has not acquired the voice signal in step S1 (step S1: No), the control apparatus 6 repeats step S1.

In a case where the result of the recognition process is an instruction (operating instruction) related to the imaging operation of the microscope apparatus 5 (step S3: Yes), the control unit 66 generates a control signal (operation control signal) according to the operating instruction, and transmits the generated signal to the control unit 5a (step S4). In a case where it is determined, as a result of the recognition process, that the input is not an operating instruction (step S3: No), the control apparatus 6 returns to step S1.

After step S4, when the communication unit 61 has acquired a voice signal (step S5: Yes), the voice recognition unit 64 performs a recognition process on the voice signal (step S6). In a case where the communication unit 61 has not acquired the voice signal in step S5 (step S5: No), the control apparatus 6 repeats step S5. In a case where the communication unit 61 has not acquired a voice signal even when a predetermined time has elapsed after step S4, the control unit 66 may display information prompting the user 101 to perform a voice input, on the display device 3. Furthermore, the control unit 66 may output from the speaker a message or an alarm sound prompting the user 101 to perform a voice input.

In a case where it is determined, as a result of the recognition process in step S6, that the voice input is an instruction to stop operation performed by the microscope apparatus 5 (for example, "stop") (step S7: Yes), the control unit 66 generates a control signal (stop control signal) to stop the operation, and transmits the generated control signal to the control unit 5a (step S8).

In a case where it is determined, as a result of the recognition process in step S6, that the voice input is not an operation stop instruction (step S7: No), the control apparatus 6 returns to step S5. In a case where no operation stop instruction has been input even when a predetermined time has elapsed after step S4, the control unit 66 may display information prompting the user 101 to perform a voice input, on the display device 3. Here, the control unit 66 may output from the speaker a message or an alarm sound prompting the user 101 to perform a voice input, as well.

After step S8, when the communication unit 61 has acquired a voice signal (step S9: Yes), the voice recognition unit 64 performs a recognition process on the voice signal (step S10). In a case where the communication unit 61 has not acquired any voice signal in step S9 (step S9: No), the control apparatus 6 repeats step S9.

In a case where the result of the recognition process in step S10 is designation of the operating state (step S11: Yes), the control unit 66 generates an operation control signal according to the designated operating state and transmits the generated signal to the control unit 5a. (Step S12). For example, in the case illustrated in FIG. 3, the control unit 66 generates a control signal to change the zoom state to class 3 and transmits the generated signal to the control unit 5a. This completes a series of the operations of the control apparatus 6.

In a case where the result of the recognition process in step S10 is not designation of the operating state (step S11: No), the control apparatus 6 returns to step S9.

Figure 7:
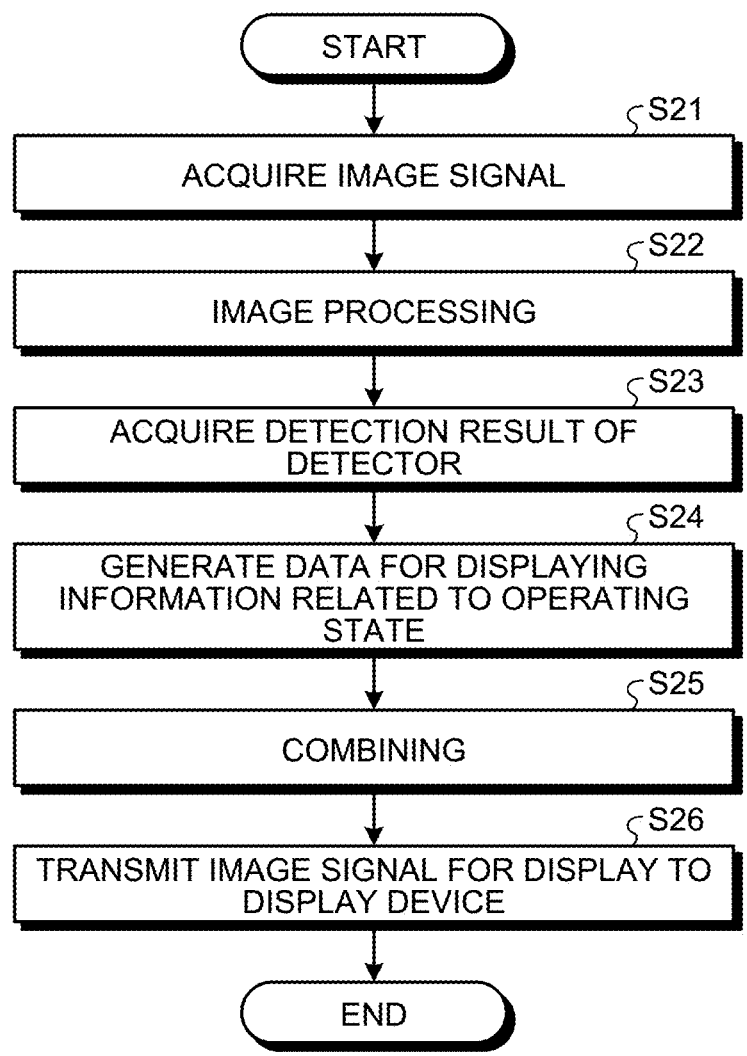
FIG. 7 is a flowchart illustrating an outline of a process of generating an image signal for display performed by an image processing unit.

FIG. 7 is a flowchart illustrating an outline of a process of generating an image signal for display performed by the control apparatus 6 when the communication unit 61 acquires an operating instruction related to the imaging operation of the microscope apparatus 5. First, the communication unit 61 acquires an image signal generated by the imaging unit 55 of the microscope apparatus 5 (step S21).

Thereafter, the image processing unit 65 performs various types of image processing described above on the acquired image signal (step S22).

Subsequently, the communication unit 61 acquires the state information detected by the detector 57 (step S23).

Thereafter, the image processing unit 65 generates data for displaying information related to the operating state (step S24). An example of this information is information indicating the classes of operating states illustrated in FIGS. 3 to 5.

Thereafter, the image processing unit 65 combines the image signal subjected to the image processing in step S22 and the data for display generated in step S24 (step S25).

Subsequently, the control unit 66 transmits the combined image signal for display to the display device 3 so as to display the signal (step S26). With this process, the images illustrated in FIGS. 3 to 5 are sequentially displayed on the display device 3, for example.

The order of processes in steps S21 to S22 and steps S23 to S24 may be reversed, or steps S21 to S22 and steps S23 to S24 may be processed in parallel.

According to the first embodiment described above, when the information carried by the voice signal is an operating instruction related to the imaging of the microscope apparatus, generation of data for displaying information related to the operating state of the microscope apparatus is performed and the generated data will be combined with an image signal to generate an image signal for display. When the information carried by the input voice signal is an instruction to stop the operation of the microscope apparatus, the operation will be stopped. In a case, after the stop, where there is a voice input of information to designate the operation state, the operating state of the microscope apparatus will be changed to the designated operating state. With these processes, it is possible to easily perform processing with a low load when a voice input of an operation instruction related to imaging is performed.

Furthermore, according to the first embodiment, with a configuration of displaying the OSD display during the operation, the user may visually inform the position desired to stop the operation, and when there is a difference between the actual stop position and the intended stop position, it is possible to return the position to the intended stop position. Therefore, it is possible to adjust to an accurate position even by using voice input.

Modification 1-1

Figure 8:
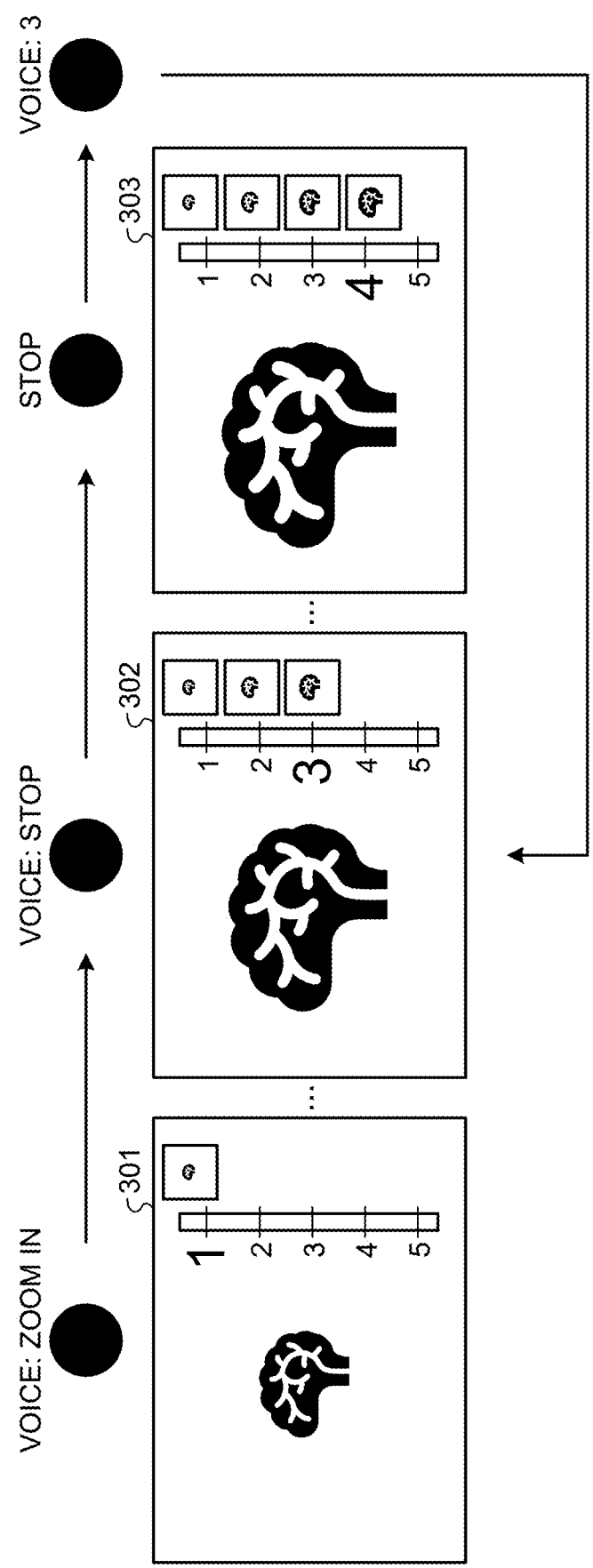
FIG. 8 is a diagram illustrating an outline of processing during a zoom operation performed by a medical observation system according to modification 1-1 of the first embodiment.

FIG. 8 is a diagram illustrating an outline of processing of a medical observation system according to modification 1-1 of the first embodiment, schematically illustrating changes in the content to be displayed on the display device 3 in a case where the zoom function of the microscope apparatus 5 is operated to increase the zoom magnification similarly to FIG. 3. In the case illustrated in FIG. 8, the position information of the zoom lens 512 is classified into classes and displayed as information related to the zoom state, and together with this, representative images captured by the microscope apparatus 5 in each of classes are displayed as thumbnail images. In other words, the image processing unit 65 generates a thumbnail image together with the class information as data for displaying information related to the operation when the class is designated by the user 101. The number of thumbnail images gradually increases with the passage of time after the zoom operation is started. For example, an image 301 having a zoom state of class 1 displays thumbnail images of class 1 alone, whereas an image 303 having a zoom state of class 4 displays four thumbnail images having zoom states of class 1 to class 4. The thumbnail image may be an image first captured by the microscope apparatus 5 in each of classes, or may be an image captured at a predetermined timing. Although here is an exemplary case where the operation of the microscope apparatus 5 is a zoom operation, the change in the content to be displayed in the case where the operation of the microscope apparatus 5 is a focus operation and a visual field movement is also similar to the above.

According to modification 1-1, by further displaying a thumbnail image as information related to the operating state, the user 101 may compare the images for individual operating states within a screen after operation stop and may select the image of the optimum operating state.

Modification 1-2

Figure 9:
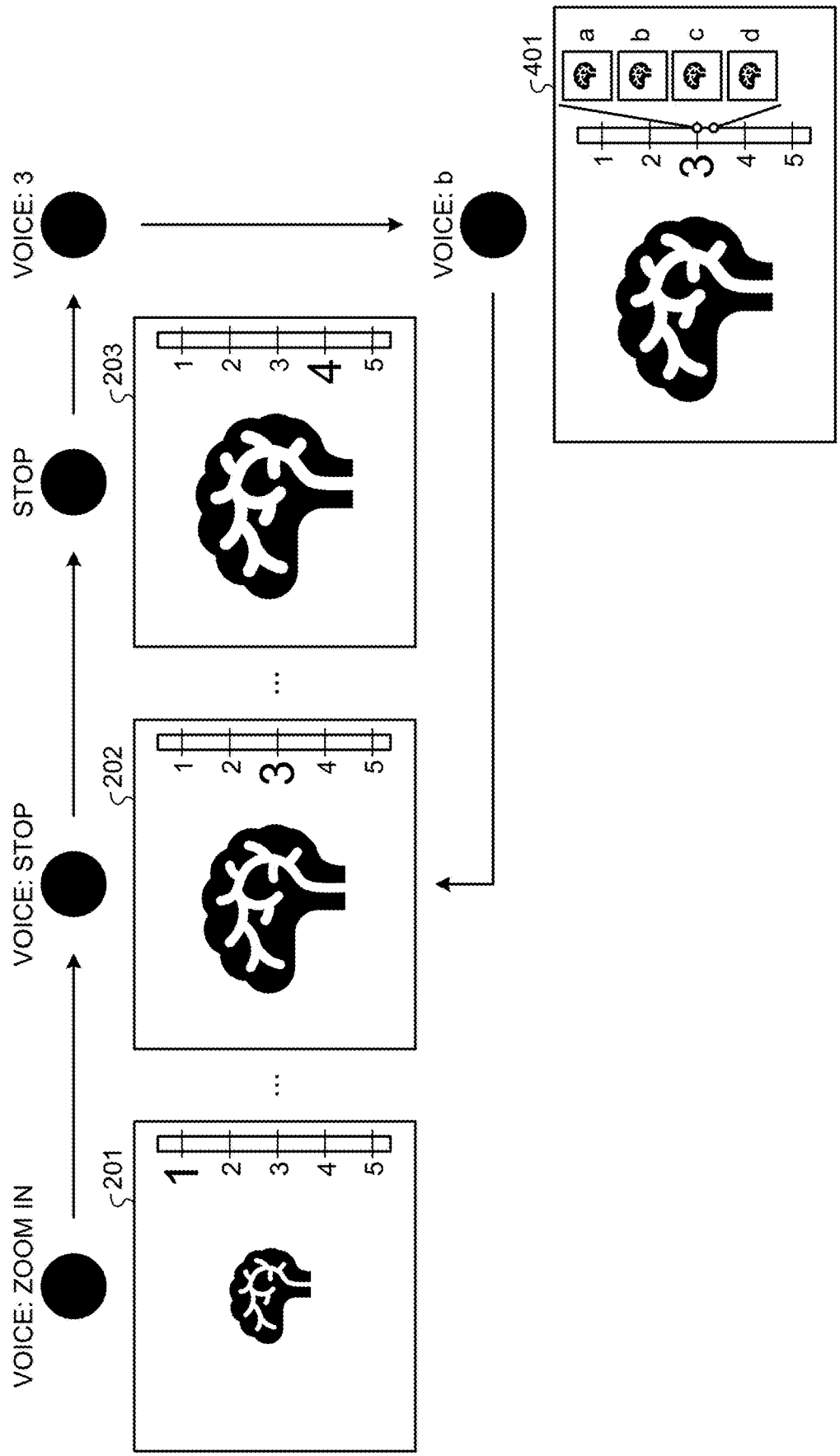
FIG. 9 is a diagram illustrating an outline of processing during a zoom operation performed by a medical observation system according to modification 1-2 of the first embodiment.

FIG. 9 is a diagram illustrating an outline of processing of a medical observation system according to modification 1-2 of the first embodiment, schematically illustrating changes in the content to be displayed on the display device 3 in a case where the zoom function of the microscope apparatus 5 is operated to increase the zoom magnification similarly to FIG. 3. In the case illustrated in FIG. 9, when the user 101 has input a desired zoom state (class 3 in FIG. 9) to the microphone 4 after stop of the operation, the display device 3 displays an image 401 including a plurality of thumbnail images included in the class. In other words, the image processing unit 65 generates at least a part of the thumbnail images included in the designated class together with the class information as data for displaying information related to the operation when the class is designated by the user 101. Note that the number of thumbnail images displayed is not limited to four, and it is possible for the user 101 to perform selection input via the input units 58, 62 or the microphone 4.

After viewing the image 401, the user 101 performs a voice input of a desired symbol among symbols (a to d) displayed next to the thumbnail images, to the microphone 4. This allows the microscope apparatus 5 to change the state to the operating state desired by the user 101 among the class 3 images. When displaying only a part of the thumbnail images of the designated class, the image processing unit 65 scrolls a part of the thumbnail images every time the user 101 inputs the class number "3" to the microphone 4 so as to generate data for display that has been replaced in sequence.

According to the present modification 1-2, the user selects an image to be viewed while viewing a plurality of candidate images of a desired class, and therefore, it is possible to quickly return to the operating state desired by the user.

Second Embodiment

The functional configuration of the medical observation system according to a second embodiment is similar to the configuration of the first embodiment. In the second embodiment, when recognizing the information carried by a voice signal, the voice recognition unit 64 determines whether or not the signal incudes a stop instruction based on a first phoneme of the voice signal. The first phoneme is "su" when the stop instruction is made in Japanese pronunciation "sutoppu", and is "s" when the stop instruction is made in English "stop", for example. In this manner, the first phoneme is different depending on the language and the word.

Furthermore, in the second embodiment, in a case where the voice recognition unit 64 has first determined that the information carried by the voice signal is an operation stop instruction based on the first phoneme of the voice signal, and thereafter has determined that the instruction is not an operation stop instruction based on the voice signal as a whole, it would be possible to return the operating state of the microscope apparatus 5 to the state before recognition made by the voice recognition unit 64 based on the first phoneme.

Figure 10:
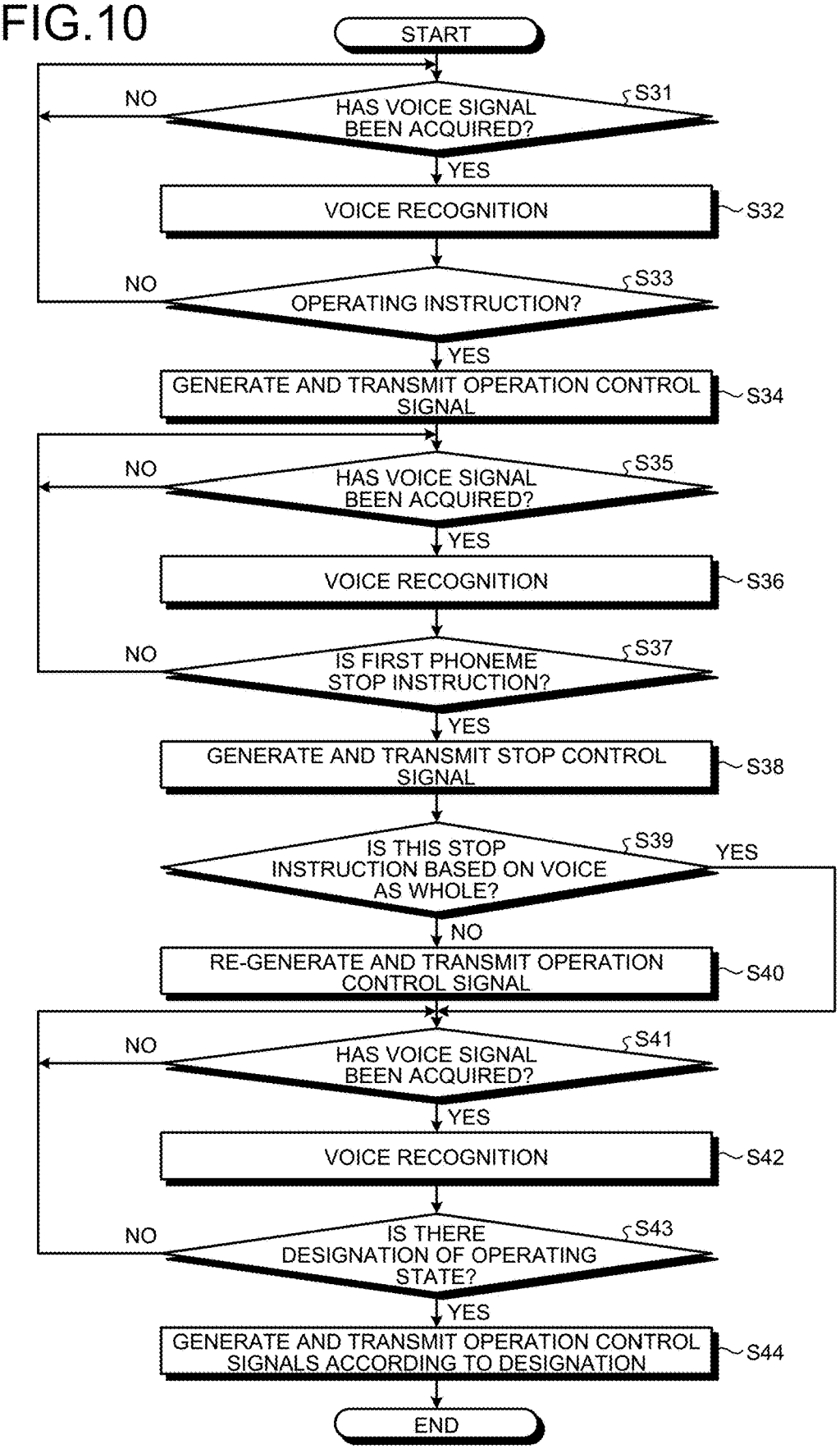
FIG. 10 is a flowchart illustrating an outline of processing of controlling a microscope apparatus performed by a control apparatus according to a second embodiment.

FIG. 10 is a flowchart illustrating an outline of a process of controlling the microscope apparatus 5 performed by the control apparatus 6 according to the second embodiment. The processes in steps S31 to S34 correspond respectively to steps S1 to S4 described in the first embodiment.

After step S34, when the communication unit 61 has acquired a voice signal (step S35: Yes), the voice recognition unit 64 performs a recognition process on the voice signal (step S36). In a case where the communication unit 61 has not acquired the voice signal in step S5 (step S5: No), the control apparatus 6 repeats step S5. In a case where the communication unit 61 has not acquired a voice signal even when a predetermined time has elapsed after step S34, the control unit 66 may display information prompting the user 101 to perform a voice input, on the display device 3. Furthermore, the control unit 66 may output from the speaker a message or an alarm sound prompting the user 101 to perform a voice input.

In a case where the first phoneme is a stop instruction (step S37: Yes) as a result of the recognition process in step S36, the control unit 66 generates a stop signal and transmits the generated signal to the control unit 5a (step S38).

Thereafter, the voice recognition unit 64 redetermines whether or not the result is a stop instruction based on the recognition result of the voice as a whole (step S39). In a case where it is determined as a stop instruction based on the voice as a whole (step S39: Yes), the control apparatus 6 proceeds to step S41. This corresponds to the case where the voice signal acquired in step S35 is "stop".

In contrast, in a case where it is determined as not a stop instruction based on the voice as a whole (step S39: No), the control unit 66 re-generates the same operation control signal as in step S34 and transmits the re-generated signal to the control unit 5a (step S40). Thereafter, the control apparatus 6 proceeds to step S41. For example, in a case where the voice signal acquired in step S35 is the "slipper" ("surippa" in Japanese pronunciation), the first phoneme is the same "su" as the "stop" ("sutoppu" in Japanese pronunciation) but is different from "stop (sutoppu)" based on the voice as a whole. In this case, the control apparatus 6 causes the microscope apparatus 5 to perform the operation once stopped.

The processes of steps S41 to S44 respectively correspond to the processes of steps S9 to S12 described in the first embodiment.

According to the second embodiment described above, when an operation instruction related to imaging is input by voice, it is possible to perform processing with a low load, similarly to the first embodiment.

Furthermore, according to the second embodiment, determination of whether or not the instruction is a stop instruction is made based on the first phoneme, making it possible to stop the operation at a timing closer to the timing desired by the user.

Modification 2-1

FIG. 11 is a diagram illustrating an outline of processing of a medical observation system according to modification 2-1 of the second embodiment, schematically illustrating changes in the content to be displayed on the display device 3 in a case where the zoom function of the microscope apparatus 5 is operated to increase the zoom magnification similarly to FIG. 3. In the modification 2-1 as well, the voice recognition unit 64 determines whether or not the voice signal is a stop instruction based on the first phoneme of the voice signal as a recognition target. In the case illustrated in FIG. 11, the voice recognition unit 64 has recognized the first phoneme "su", resulting in the stop of the operation of the microscope apparatus 5 under the control of the control unit 66. Thereafter, the display device 3 displays a plurality of thumbnail images including images of the same class as the stop position of the operation and images up to a predetermined number of images returned from the stop position. In other words, after the stop of operation of the microscope apparatus 5, the image processing unit 65 generates a plurality of thumbnail images of the same class as the stop position and including images up to a predetermined number of images returned from the stop position, as data for display, together with the class information. After viewing this image, the user 101 performs a voice input of a desired symbol among the symbols (a to d) displayed next to the thumbnail images to the microphone 4. FIG. 11 illustrates the case where the symbol "b" is input. In this case, the microscope apparatus 5 changes to the operating state corresponding to the symbol b in the class 3 image.

According to modification 2-1, a plurality of thumbnail images are displayed on the display device 3 at a point of stop of the operation of the microscope apparatus 5. This makes it possible to quickly return to the operating state desired by the user.

Other Embodiments

Embodiments have been described hereinabove, however, the present disclosure is not intended to be limited to the above-described first to two embodiments. For example, when the image processing unit 65 generates data for displaying information indicating the operating state of the imaging device, it is allowable to set the range (scale size) of one class and the number of classes based on the depth of focus corresponding to the zoom magnification and an aperture value of the microscope apparatus 5. Specifically, it is allowable to set approximately ¼ to ½ of the depth of focus as the class range.

Furthermore, when the image processing unit 65 generates data for displaying information indicating the operating state of the imaging device, it is allowable to set the range (scale size) of one class and the number of classes based on user's usage history (including operation history) of the microscope apparatus 5.

Furthermore, when the image processing unit 65 displays the thumbnail image of the designated class, it is allowable to set the number of thumbnail images to be displayed, based on the user's usage history (including the operation history). For example, the storage unit 67 may store the average number of thumbnail images viewed before the user selects one image, and the image processing unit 65 may set the number of thumbnail images to be displayed for each of users based on the data so as to generate the data for display.

Furthermore, the medical observation apparatus according to the present disclosure may be an endoscope or an exoscope equipped with an imaging device.

The present technology may also have the following configurations.

(1)
A control apparatus including
circuitry configured to:
acquire an image signal generated by an imaging device configured to image an observation target;
acquire an operation instruction made by a voice input;
control a display device to display a plurality of images generated based on the image signal corresponding to an operating state of the imaging device, together with information related to the operating state, in a case where the operation instruction is an operation instruction related to imaging of the imaging device; and
control to change the imaging device to an operating state corresponding to the image selected by a user among the plurality of images.

(2)
The control apparatus according to (1), wherein
the operation instruction is a voice signal generated by a microphone configured to receive a voice input, and the circuitry is configured to
recognize information carried by the voice signal,
stop an operation in a case where the recognized information is an instruction to stop the operation, and
change the imaging device to the operating state designated by the voice signal in a case where the recognized information after stop of the operation is information designating the operating state.

(3)

The control apparatus according to (1) or (2), wherein the information related to the operating state includes information related to a position of an operating target.

(4)

The control apparatus according to any one of (1) to (3), wherein the information related to the operating state includes information related to positions of an operating target, and a thumbnail image representing each of the positions.

(5)

The control apparatus according to any one of (1) to (4), wherein, in a case where an operating state has been designated by the operation instruction, the circuitry is configured to control the display device to display a plurality of thumbnail images corresponding to the operating state.

(6)

The control apparatus according to any one of (1) to (5), wherein the circuitry is further configured to set a display mode of information related to an operating state of the imaging device based on a depth of focus according to imaging conditions of the imaging device.

(7)

The control apparatus according to any one of (1) to (6), wherein the circuitry is further configured to set a display mode of information related to an operating state of the imaging device based on a usage history of the imaging device by a user of the imaging device.

(8)

The control apparatus according to (2), wherein the circuitry is configured to determine whether or not the information carried by the voice signal is an instruction to stop the operation based on a first phoneme of the voice signal.

(9)

The control apparatus according to (8), wherein, in a case where the circuitry has first determined that the information carried by the voice signal is an instruction to stop the operation based on the first phoneme of the voice signal and has thereafter determined that the information carried by the voice signal is not the instruction to stop the operation based on the voice signal as a whole, the circuitry is configured to control to return the operating state of the imaging device to a state before the recognition made by the circuitry based on the first phoneme.

(10)

The control apparatus according to any one of (1) to (9), wherein the operation instruction related to the imaging of the imaging device is an operating instruction in any of focus, zoom, and visual field movement.

(11)

A medical observation system including:
an imaging device configured to image an observation target and generate an image signal;
a display device configured to display an image; and
a control apparatus including
a circuitry configured to
acquire the image signal generated by the imaging device,
acquire an operation instruction made by a voice input,
control the display device to display a plurality of images generated based on the image signal corresponding to an operating state of the imaging device, together with information related to the operating state, in a case where the operation instruction is an operation instruction related to imaging of the imaging device, and
control to change the imaging device to an operating state corresponding to the image selected by a user among the plurality of images.

Supplementary Note 1

A control apparatus including:
an acquisition unit configured to acquire a voice signal generated by a microphone that receives an input of voice instructing an operation of an imaging device that images an observation target; and
a voice recognition unit configured to determine whether or not information carried by the voice signal is an instruction to stop an operation of the imaging device based on a first phoneme of the voice signal acquired by the acquisition unit.

Supplementary Note 2

The control apparatus according to Supplementary note 1, including a control unit configured to stop the operation in a case where the voice recognition unit has determined that the information carried by the voice signal is an instruction to stop the operation based on the first phoneme of the voice signal, and configured to return an operating state of the imaging device to a state before a recognition made by the voice recognition unit in a case where, after the determination, the voice recognition unit determines that the information carried by the voice signal is not the instruction to stop the operation based on the voice signal as a whole.

Supplementary Note 3

A medical observation system including:
an imaging device configured to image an observation target and generate an image signal;
a microphone configured to receive a voice input and generate a voice signal;
a display device configured to display an image; and
a control apparatus including
an acquisition unit configured to acquire a voice signal generated by the microphone configured to receive a voice input instructing an operation of the imaging device that images an observation target, and
a voice recognition unit configured to determine whether or not the information carried by the voice signal is an instruction to stop an operation of the imaging device based on a first phoneme of the voice signal acquired by the acquisition unit.

According to the present disclosure, when an operation instruction related to imaging is input by voice, it is possible to perform processing with a low load.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A control apparatus comprising
circuitry configured to:
acquire an image signal generated by an imaging device configured to image an observation target;
acquire an operation instruction made by a voice input;

control a display device to display a plurality of images generated based on the image signal corresponding to an operating state of the imaging device, together with information related to the operating state, in a case where the operation instruction is an operation instruction related to imaging of the imaging device;

control to change the imaging device to an operating state corresponding to the image selected by a user among the plurality of images, wherein the operation instruction is a voice signal generated by a microphone configured to receive a voice input;

recognize information carried by the voice signal, determine whether or not the information carried by the voice signal is an instruction to stop the operation based on a first phoneme of the voice signal;

stop an operation in a case where the recognized information is an instruction to stop the operation; and change the imaging device to the operating state designated by the voice signal in a case where the recognized information after stop of the operation is information designating the operating state.

2. The control apparatus according to claim 1, wherein the information related to the operating state includes information related to a position of an operating target.

3. The control apparatus according to claim 1, wherein the information related to the operating state includes information related to positions of an operating target, and a thumbnail image representing each of the positions.

4. The control apparatus according to claim 1, wherein, in a case where an operating state has been designated by the operation instruction, the circuitry is configured to control the display device to display a plurality of thumbnail images corresponding to the operating state.

5. The control apparatus according to claim 1, wherein the circuitry is further configured to set a display mode of information related to an operating state of the imaging device based on a depth of focus according to imaging conditions of the imaging device.

6. The control apparatus according to claim 1, wherein the circuitry is further configured to set a display mode of information related to an operating state of the imaging device based on a usage history of the imaging device by a user of the imaging device.

7. The control apparatus according to claim 1, wherein, in a case where the circuitry has first determined that the information carried by the voice signal is an instruction to stop the operation based on the first phoneme of the voice signal and has thereafter determined that the information carried by the voice signal is not the instruction to stop the operation based on the voice signal as a whole, the circuitry is configured to control to return the operating state of the imaging device to a state before the recognition made by the circuitry based on the first phoneme.

8. The control apparatus according to claim 1, wherein the operation instruction related to the imaging of the imaging device is an operating instruction in any of focus, zoom, and visual field movement.

9. A medical observation system comprising:
an imaging device configured to image an observation target and generate an image signal;
a display device configured to display an image; and
a control apparatus including
a circuitry configured to
acquire the image signal generated by the imaging device,
acquire an operation instruction made by a voice input,
control the display device to display a plurality of images generated based on the image signal corresponding to an operating state of the imaging device, together with information related to the operating state, in a case where the operation instruction is an operation instruction related to imaging of the imaging device,
control to change the imaging device to an operating state corresponding to the image selected by a user among the plurality of images, wherein the operation instruction is a voice signal generated by a microphone configured to receive a voice input;
recognize information carried by the voice signal, determine whether or not the information carried by the voice signal is an instruction to stop the operation based on a first phoneme of the voice signal;
stop an operation in a case where the recognized information is an instruction to stop the operation; and
change the imaging device to the operating state designated by the voice signal in a case where the recognized information after stop of the operation is information designating the operating state.

10. The medical observation system according to claim 9, wherein, in a case where the circuitry has first determined that the information carried by the voice signal is an instruction to stop the operation based on the first phoneme of the voice signal and has thereafter determined that the information carried by the voice signal is not the instruction to stop the operation based on the voice signal as a whole, the circuitry is configured to control to return the operating state of the imaging device to a state before the recognition made by the circuitry based on the first phoneme.

11. The medical observation system according to claim 9, wherein, in a case where an operating state has been designated by the operation instruction, the circuitry is configured to control the display device to display a plurality of thumbnail images corresponding to the operating state.

12. The medical observation system according to claim 11, wherein a number of thumbnail images displayed increases after the operation is started.

13. The control apparatus according to claim 4, wherein a number of the plurality of thumbnail images displayed increases after the operation is started.

14. A control method, comprising
acquiring an image signal generated by an imaging device configured to image an observation target;
acquiring an operation instruction made by a voice input;
displaying a plurality of images generated based on the image signal corresponding to an operating state of the imaging device, together with information related to the operating state, in a case where the operation instruction is an operation instruction related to imaging of the imaging device;
controlling to change the imaging device to an operating state corresponding to the image selected by a user among the plurality of images, wherein the operation instruction is a voice signal generated by a microphone configured to receive a voice input;
recognizing information carried by the voice signal, determine whether or not the information carried by the voice signal is an instruction to stop the operation based on a first phoneme of the voice signal;

stopping an operation in a case where the recognized information is an instruction to stop the operation; and changing the imaging device to the operating state designated by the voice signal in a case where the recognized information after stopping the operation is information designating the operating state.

15. The control method according to claim 14, wherein, in a case where the information carried by the voice signal is determined to be an instruction to stop the operation based on the first phoneme of the voice signal and has thereafter determined that the information carried by the voice signal is not the instruction to stop the operation based on the voice signal as a whole, returning the operating state of the imaging device to a state before the recognition is made based on the first phoneme.

16. The control method according to claim 14, further comprising setting display mode of information related to an operating state of the imaging device based on a depth of focus according to imaging conditions of the imaging device.

17. The control method according to claim 14, further comprising setting a display mode of information related to an operating state of the imaging device based on a usage history of the imaging device by the user of the imaging device.

18. The control method according to claim 14, wherein, in a case where an operating state has been designated by the operation instruction, displaying a plurality of thumbnail images corresponding to the operating state.

19. The control method according to claim 18, wherein a number of thumbnail images displayed increases after the operation is started.

* * * * *